United States Patent [19]

Vayenas et al.

[11] 4,329,208

[45] May 11, 1982

[54] METHOD AND APPARATUS FOR CONVERTING ETHYLENE TO ETHYLENE OXIDE

[75] Inventors: Costas G. Vayenas, Wellesley Hills; Michael Stoukides, Cambridge, both of Mass.

[73] Assignee: Massachusetts Institute of Technology, Cambridge, Mass.

[21] Appl. No.: 225,542

[22] Filed: Jan. 16, 1981

[51] Int. Cl.³ .................... H01M 8/10; H01M 8/22; C25B 3/02; C07D 301/04
[52] U.S. Cl. .................................. 204/59 R; 204/80; 429/12; 429/33; 429/40
[58] Field of Search ................ 204/59 R, 80; 429/33, 429/40

[56] References Cited

U.S. PATENT DOCUMENTS 3,138,487  6/1964  Tragert ................................ 429/33
3,288,692  11/1966  Leduc .................................. 204/80
3,436,268  4/1969  Satterfield et al. ............... 429/33 X
3,497,431  2/1970  Kronig et al. ....................... 204/80

FOREIGN PATENT DOCUMENTS 1508923  1/1968  France ................................ 204/80

*Primary Examiner*—F. Edmundson
*Attorney, Agent, or Firm*—Arthur A. Smith, Jr.; Paul J. Cook

[57] ABSTRACT

Ethylene oxide is formed by the oxidation of ethylene. An ethylene-containing gas is contacted with an oxidation catalyst deposited on the surface of a solid electrolyte while an oxygen-containing gas contacted with a second catalyst capable of dissociating oxygen gas to oxygen ion deposited upon a second surface of the solid electrolyte. Oxygen ions are transported under a positive voltage applied through the solid electrolyte to react with ethylene to form ethylene oxide.

7 Claims, 14 Drawing Figures

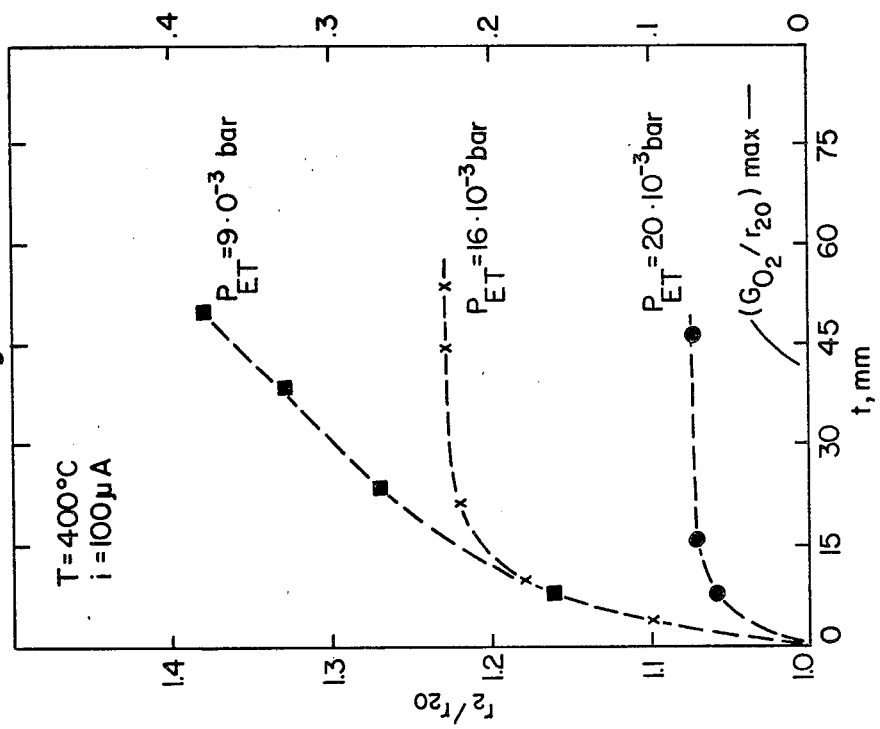
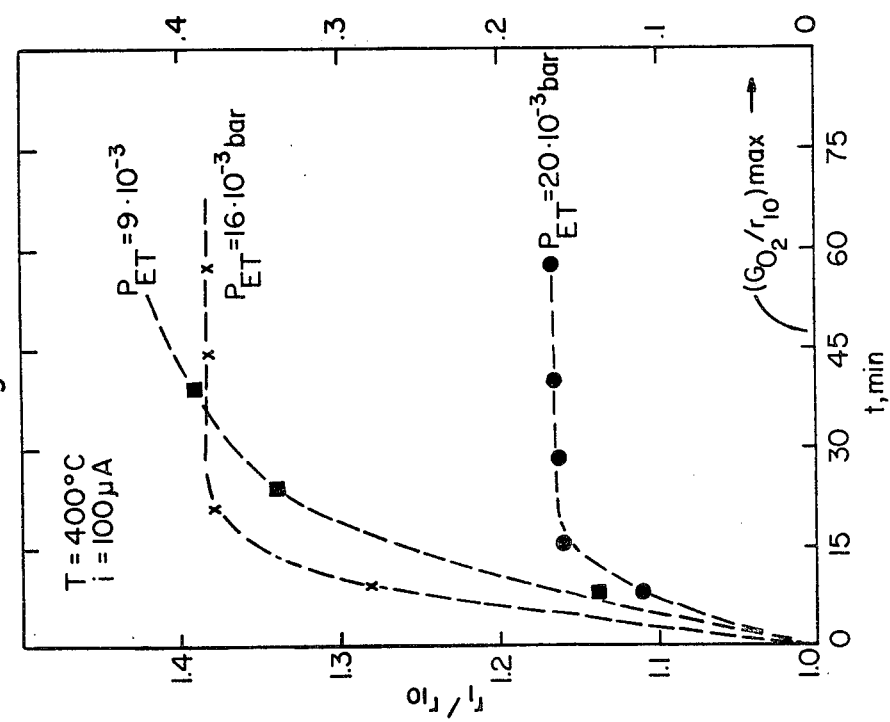

METHOD AND APPARATUS FOR CONVERTING ETHYLENE TO ETHYLENE OXIDE

The Government has rights in this invention pursuant to Grant Numbers ENG 77-27500 and IPA-0010 awarded by the National Science Foundation.

BACKGROUND OF THE INVENTION

This invention relates to a method and apparatus for oxidizing ethylene to form ethylene oxide.

Ethylene oxide is widely utilized in many applications such as for sterilizing medical materials or as a precursor for forming polymers such as poly(ethylene oxide). The oxidation of ethylene is conducted in the presence of a silver or silver alloy catalyst on a support such as alumina. Chlorinated hydrocarbons frequently are added to the gas phase in trace amounts to increase selectively of the reaction to ethylene oxide. Maximum selectivity is achieved commercially at temperatures between about 230° C. and 280° C. and is approximately 80% mole ethylene oxide produced/moles ethylene reacted. It would be desirable to provide a process capable of having improved conversion of ethylene to ethylene oxide while minimizing production of carbon dioxide.

SUMMARY OF THE INVENTION

This invention provides a means for oxidizing ethylene to form ethylene oxide selectively and comprises a plurality of electrolytic cells. Each cell comprises a solid electrolyte capable of transporting oxygen ion which electrolyte is coated on opposing surfaces with a first catalyst and a second catalyst. The first catalyst which is capable of dissociating oxygen gas into oxygen ions is contacted with a stream of oxygen-containing gas. The second catalyst is capable of promoting the oxidation of ethylene and is contacted with an ethylene- and oxygen-containing feed stream. The solid electrolyte coated with the catalysts is subjected to a electrical voltage in order to increase the passage of oxygen ions therethrough. The oxygen ions pass through the solid electrolyte into the second catalyst and are reacted with ethylene to form the ethylene oxide and carbon dioxide. The ethylene-containing gas is pre-heated to a temperature so that the oxidation reaction can be initiated and maintained. By virtue of the voltage applied to the two catalysts and solid electrolyte, the rate of conversion of ethylene to ethylene oxide is far greater than the rate of transport of oxygen ion through the electrolyte resulting from the applied voltage.

This invention provides substantial operating advantages over the prior art techniques for oxidizing ethylene to form ethylene oxide. The primary advantage is that the process of this invention effects a substantially increased production of ethylene oxide when voltage is applied to the solid electrolyte as compared to the cost of the electrical energy utilized.

BRIEF DESCRIPTION OF THE DRAWINGS

FIG. 2 shows the effect on ethylene oxide production of ethylene pressure when a current $i = 100$ $\mu A$ is applied at time zero.

FIG. 3 shows the effect on carbon dioxide production of ethylene pressure when a current i-100 $\mu A$ is applied at time zero.

DETAILED DESCRIPTION OF SPECIFIC EMBODIMENTS

Figure 1:
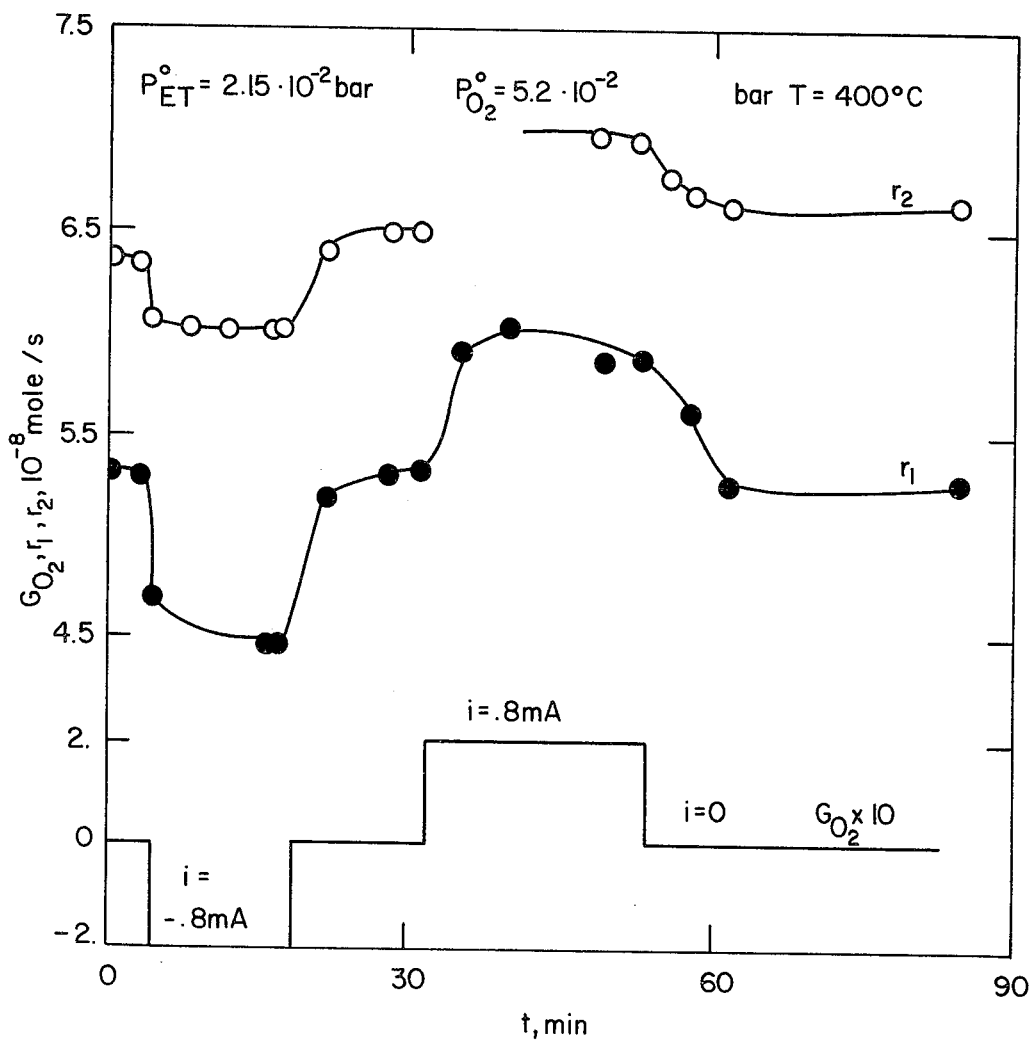
FIG. 1 shows the effect of voltage on ethylene oxide production and $CO_2$ production.

This invention provides an apparatus for effecting oxidation of ethylene which comprises at least one solid electrolyte capable of transporting oxygen ion; each solid electrolyte being coated on one side with a first catalyst material capable of dissociating oxygen to form oxygen ion. Each solid electrolyte also is coated on a second surface with a catalytic material capable of promoting the oxidation of ethylene. Feed gases are introduced into the reactor so that an oxygen-containing feed gas contacts the first catalyst while an ethylene-containing feed gas contacts the second catalyst. In addition, sealing means are provided so that the oxygen-containing gas and the ethylene-containing gas are not admixed. Oxidation of the ethylene occurs adjacent the second catalyst to form ethylene oxide which then is recovered from the ethylene-containing gas. The elements comprising the solid electrolyte are formed in a manner so as to define channels which are exposed only to either the first catalyst or to the second catalyst and so that channels exposed only to the first catalyst are positioned adjacent channels exposed only to the second catalyst. Thus, oxygen converted to oxygen ions by virtue of contact with the first catalyst migrate through the solid electrolyte to contact the second catalyst which promotes ethylene oxidation. For example, the solid electrolyte can be in the form of hollow tubes, the inner surface of which is coated with one catalyst while the outer surface tube is coated with the second catalyst. Alternatively, the solid electrolyte can be formed into thin plates which are arranged within a reactor shell to form channels as described above.

Reaction to form ethylene oxide occurs within the portions of the reactor to which has been introduced the ethylene-containing feed gas. Generally, reaction occurs at a temperature between about 200° C. and about 450° C., preferably between about 250° C. and about 330° C. It is desirable to maintain the temperature below 400° C. in order to substantially reduce the formation of carbon dioxide. It is also desirable to effect the conversion above about 250° C. in order to maintain currents of at least 10 $\mu$A through the electrolyte. Generally, reaction can be effected in the presence of an inert diluting gas and/or up to 20 volume percent oxygen admixed with ethylene feed gas in order to improve yield of ethylene oxide. Suitable inert gases include helium, argon or the like. Generally, dilution can be effected so that the resultant diluted gas contains between about 2 and 80 volume percent ethylene based upon the total volume of the ethylene-containing feed gas.

Any solid electrolyte capable of transporting oxygen ions under the reaction conditions suitable for forming ethylene oxide from ethylene can be utilized herein. Typically, oxygen ion conducting solid electrolytes are solid solutions formed between oxides containing divalent and trivalent cation such as $CaO$, $Sc_2O_3$, $Y_2O_3$, $La_2O_3$ or the like with oxides containing tetravalent cations such as $ZrO_2$, $ThO_2$ and $CeO_2$. Their higher ionic conductivity is due to the existence of $O^=$ site vacancies. One $O^=$ vacancy occurs for each divalent or each two trivalent cations that are substituted for a tetravalent ion in the lattice. Of particular interest is a solid solution containing about 15 mol percent $CaO$ in $ZrO_2$ (calcia stabilized zirconia) or a solid solution containing about 8 mol percent $Y_2O_3$ in $ZrO_2$ (yttria stabilized zirconia). These latter two solid electrolytes are characterized by their high ionic conductivity, their pure oxygen ion conduction over wide ranges of temperature and oxygen pressure and their relatively low cost.

Representative catalytic materials useful for decomposing oxygen to oxygen ion are platinum, platinum-rhodium alloy, gold, silver or the like. Representative suitable catalysts useful for promoting the oxidation of ethylene to ethylene oxide include silver or silver alloys. The catalyst composition can be deposited on the solid electrolyte by any conventional means including precipitation from solution, paste application or vapor deposition. The preferred catalyst to effect oxygen ion formation comprises a platinum-rhodium alloy containing between about five and fifteen weight percent rhodium since this catalyst is effective in promoting the desired reactions and is capable of withstanding the reaction conditions encountered over long periods of time. The rhodium provides little catalytic activity but serves to stabilize the platinum under the reaction conditions. The preferred catalyst for promoting ethylene oxide production is silver.

The present invention provides advantages over present processes in that it is capable of producing ethylene oxide at higher yields with low side oxidation reaction to undesirable by-products such as ethylene oxide.

Figure 5:
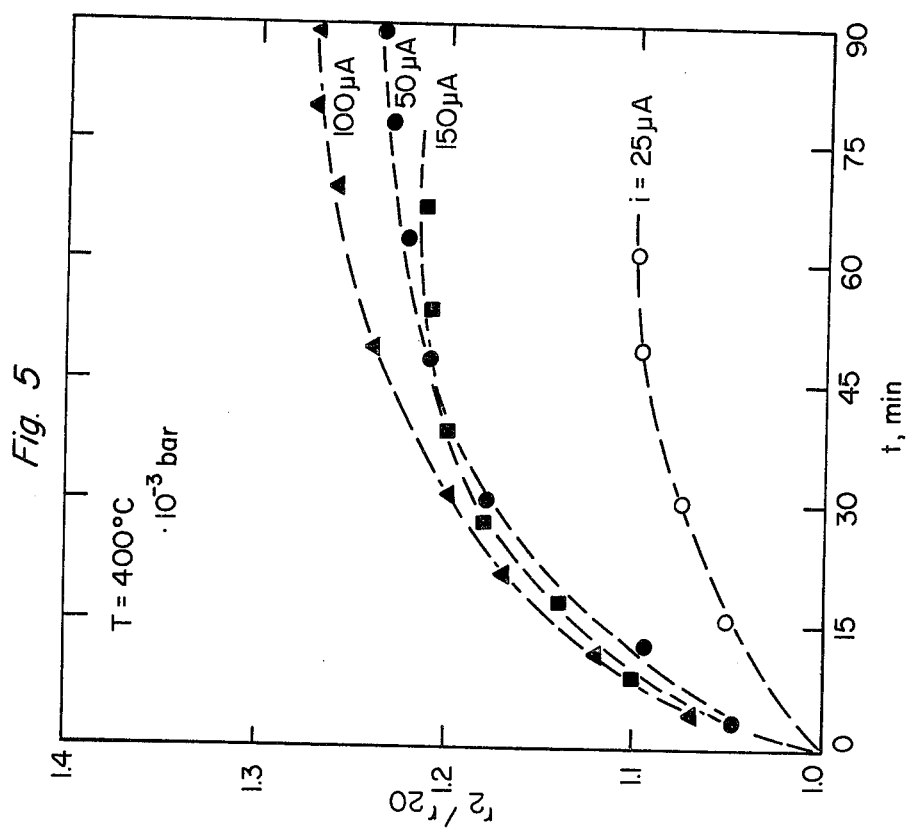
FIG. 5 shows the effect of current on carbon dioxide production when the current is applied at time zero.
Figure 4:
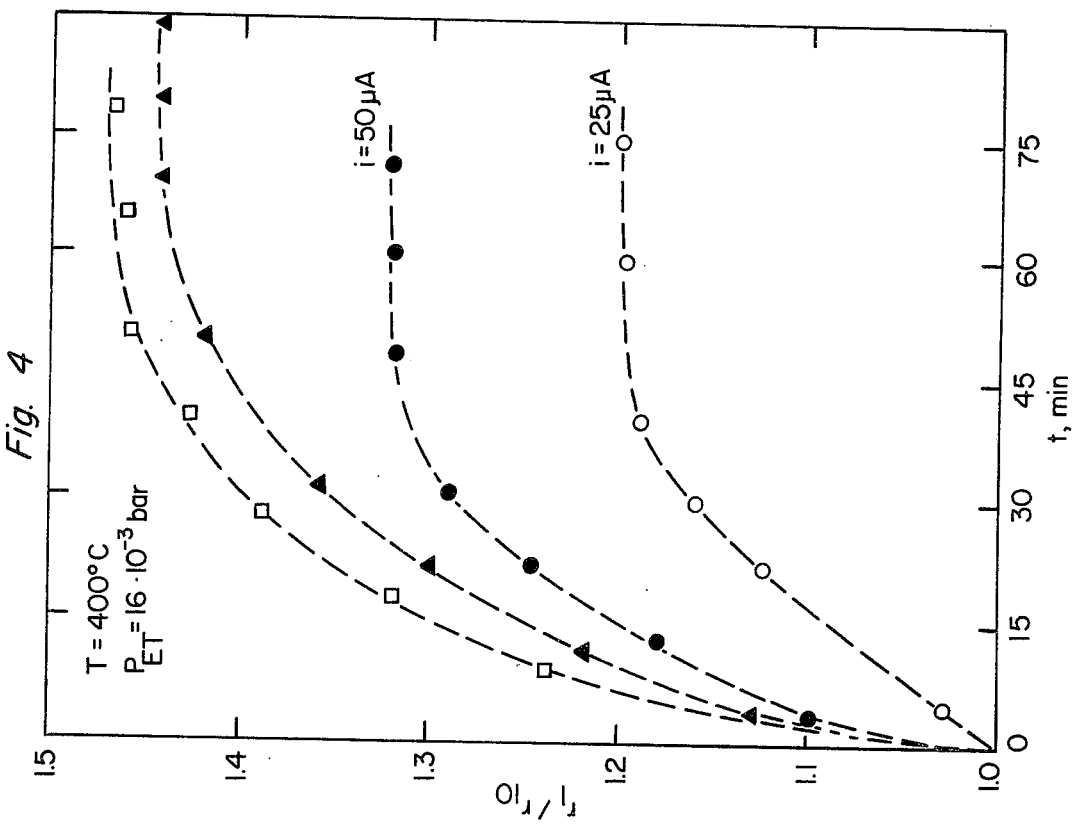
FIG. 4 shows the effect of current on ethylene oxide production when the current is applied at time zero.
Figure 6:
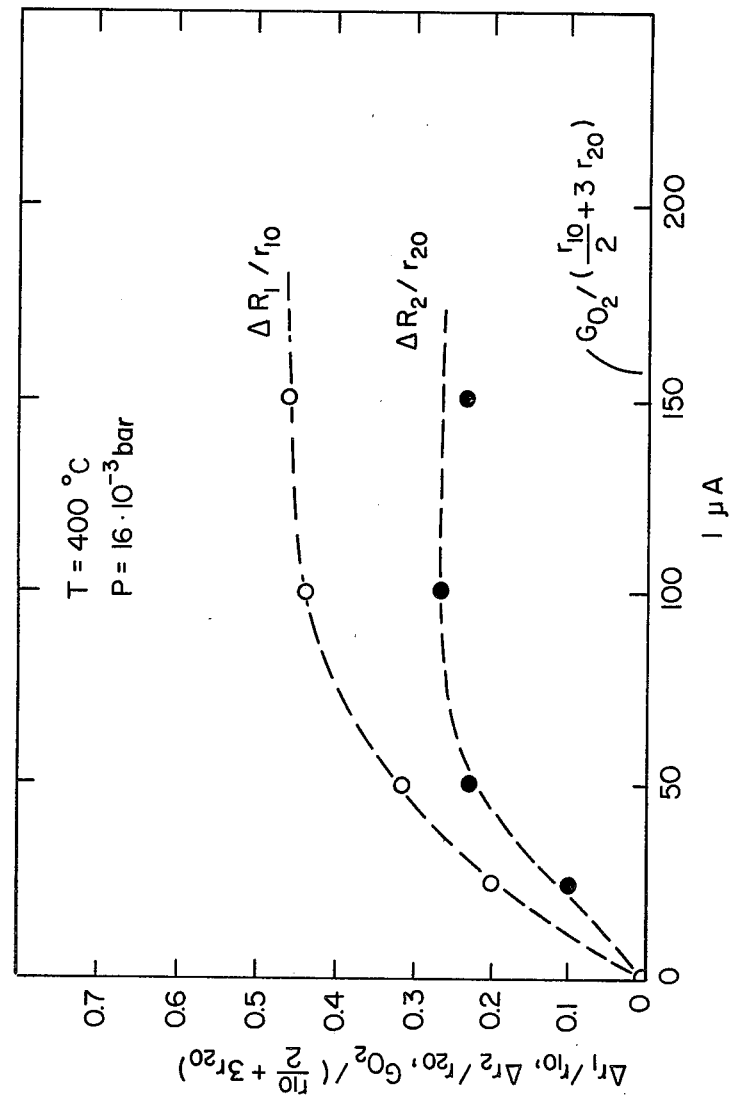
FIG. 6 shows the steady state effect of applied current on the ethylene oxide and carbon dioxide production.

FIG. 1 shows the effect of oxygen pumping under the influence of a current. $G_{O2}$ is the flux of oxygen through the solid electrolyte. $r_1$ is the rate of ethylene oxide production. $r_2$ is the rate of carbon dioxide production. $G_{O2} = (i/4F)$ wherein F is the Faraday constant and i is the current in milliamps. The positive current (0.8 mA) corresponds to oxygen ion "pumped" to the catalyst which promotes ethylene oxide production. A negative current corresponds to oxygen ion "pumped" from the catalyst which decreases ethylene oxide production. As shown in FIG. 1, the changes in the rate of ethylene oxide production and the rate of carbon dioxide production are about 12 times larger each than $G_{O2}$. This amplification can be as large as a factor of 300 or more. In FIG. 1, it is only 12 times because the current used is large ($\pm 0.8$ mA). As shown in FIGS. 4, 5 and 6, the same effect can be achieved with much smaller currents.

FIG. 2 shows the transient behavior of the reaction with a constant current of $+100$ $\mu$A which is applied at the starting time $t_0$. The rate of ethylene oxide production before applying current is $r_{10}$. The rate of ethylene oxide production is $r_1$. There is a huge difference (a factor of about 300) between $r_1/r_{10}$ and the maximum anticipated increase in $r_1$ (i.e. $G_{O2}/r_{10}$) when only the oxygen pumped through the electrolyte is reacting.

FIG. 3 shows the transient behavior as shown in FIG. 2 except for the effect on the rate of carbon dioxide production ($r_2$).

FIG. 4 shows the transient behavior of the ethylene oxide reaction when different currents, i, are applied constantly starting at a time $t=0$.

FIG. 5 shows the transient behavior with different current on the production of carbon dioxide.

FIG. 6 shows the steady state effect on $r_1$ and $r_2$ as a function of applied current. These curves show a comparison with maximum anticipated rate increase when only the oxygen "pumped" through the electrolyte were reacting. As shown in this figure, the intrinsic catalytic properties of the silver catalyst are modified due to the oxygen "pumping" and/or due to the voltage applied.

Figure 7:
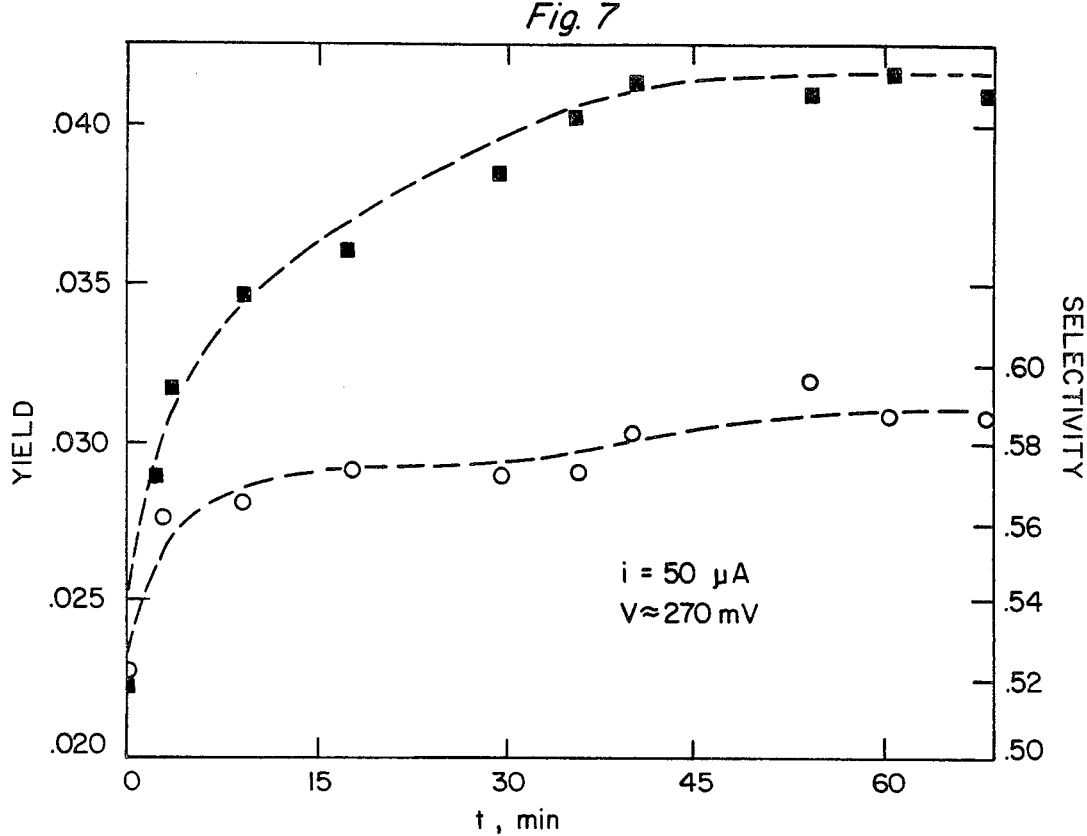
FIG. 7 shows the effect of oxygen pumping to the catalyst that promotes ethylene oxide production.

FIG. 7 shows the transient effect of oxygen pumping to the silver catalyst at a current of $+50$ $\mu$A on selectivity and yield at a temperature of 400° C.

Figure 8:
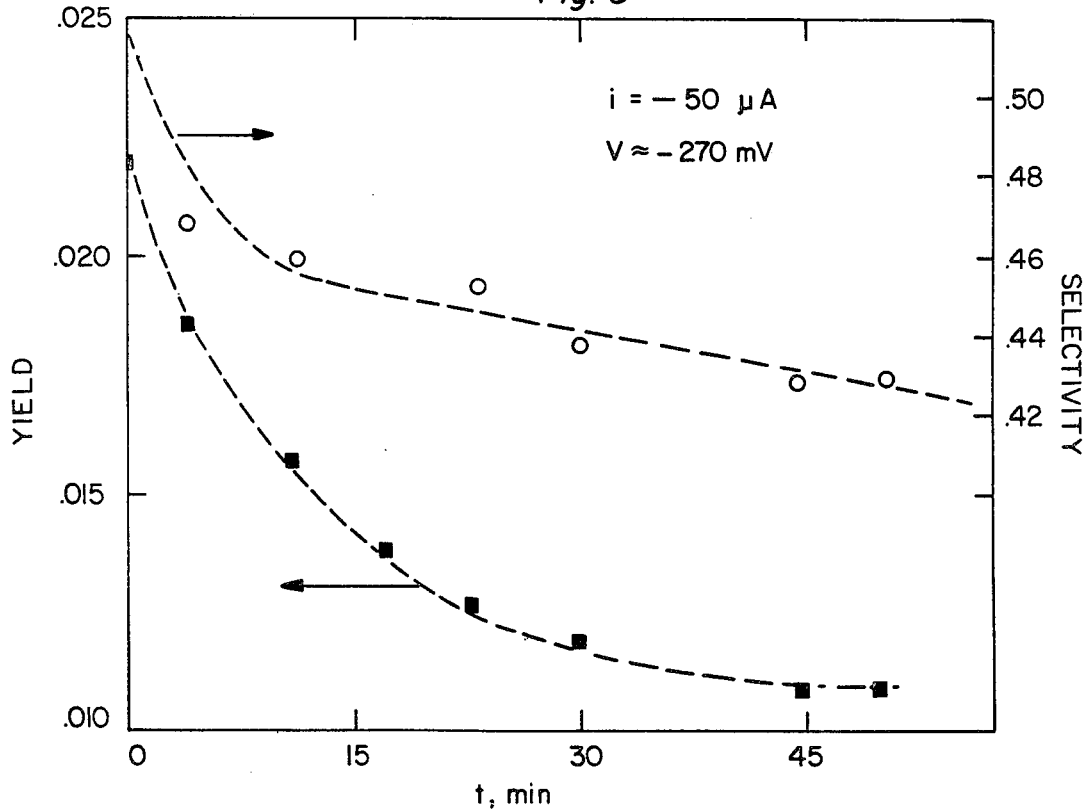
FIG. 8 shows the effect of oxygen pumping from the catalyst that promotes carbon dioxide production.

FIG. 8 shows the transient effect of oxygen pumping from the silver catalyst at a current of $-50$ $\mu$A on selectivity and yield at a temperature of 400° C.

Figure 9:
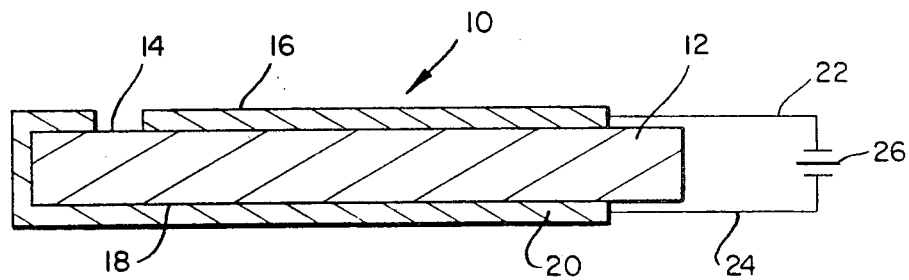
FIG. 9 is a side view, in cross-section of an apparatus suitable for carrying out the process of this invention.

Referring to FIG. 9, a coated solid electrolyte useful in the process and apparatus of this invention is shown. As shown, the active element 10 comprises a core 12 formed of the solid electrolyte which is coated on one surface 14 with a catalyst 16 useful for converting oxygen gas to oxygen ion. The solid electrolyte 12 is coated on a second surface 18 with a second catalyst 20 which promotes the oxidation of ethylene to form ethylene oxide. An electrical lead 22 is connected to catalyst 16 and electrical lead 24 is connected to catalyst 20 in order to apply voltage to the solid electrolyte. Oxygen gas which contacts catalyst 16 is converted to oxygen ion which migrates through solid electrolyte 12 to contact catalyst 20. At the surface of catalyst 20, the oxygen ion is converted to oxygen gas and reacts with the ethylene contacting catalyst 20 to form ethylene oxide. During this reaction, the oxygen ion gives up two electrons which travel through the circuit formed by lead 24, battery 26 and lead 22 back to catalyst 16.

Figure 10:
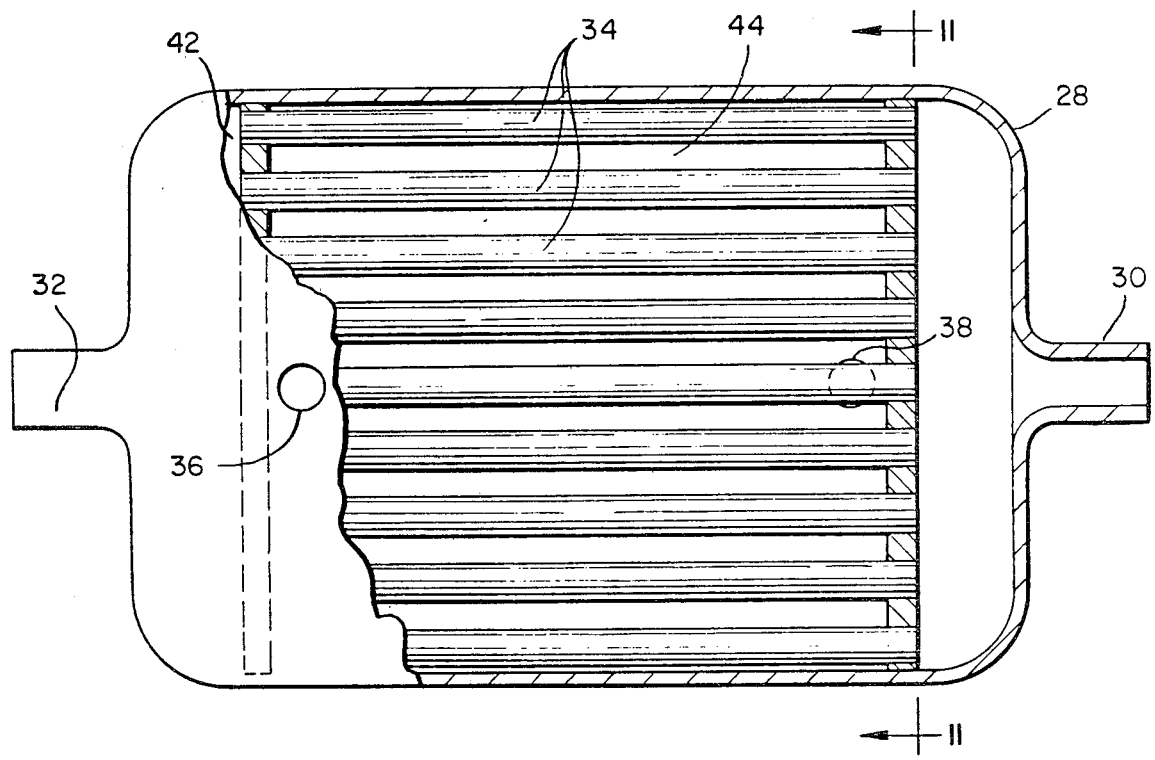
FIG. 10 is a cross-sectional view taken along line 10-10 of FIG. 9.
Figure 11:
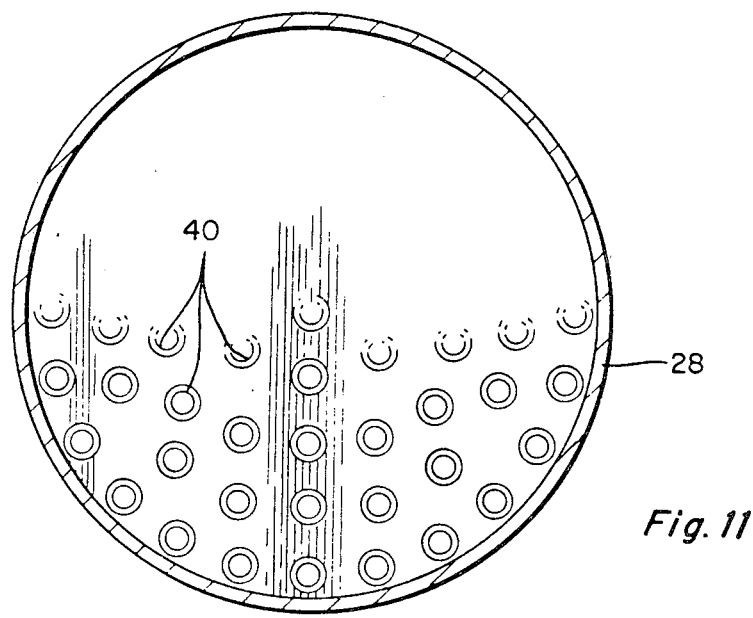
FIG. 11 is a side view, in cross-section of an alternative reactor means for carrying out the process of this invention.

The reactor apparatus shown in FIGS. 10 and 11 comprises a shell 28 having an inlet 30 and an outlet 32. Within the shell 28 are located a plurality of tubes 34 formed from a solid electrolyte capable of transporting oxygen ions. The interiors of tubes 34 are coated with a catalyst suitable for converting oxygen gas to oxygen ion while the exterior of tubes 34 are coated with a catalyst suitable for promoting the oxidation of ethylene to form ethylene oxide. The shell 28 is provided with a second inlet 36 and a second outlet 38 which second inlet and second outlet comprise the means for introducing an ethylene-containing gas into the shell 28 to contact the exterior of tubes 34. The inlet 30 and the outlet 32 are adapted to permit passage of an oxygen-containing gas such as air into the plenum 38 through the tube inlets 40, into plenum 42 and out through outlet 32. The second inlet 36 and the second outlet 38 are adapted to permit passage of an ethylene-containing gas into chamber 44 to contact the second catalyst coated on the outer surface of tubes 34 thereby to effect production of ethylene oxide which is then removed from the reactor through a second outlet 38.

Figure 12:
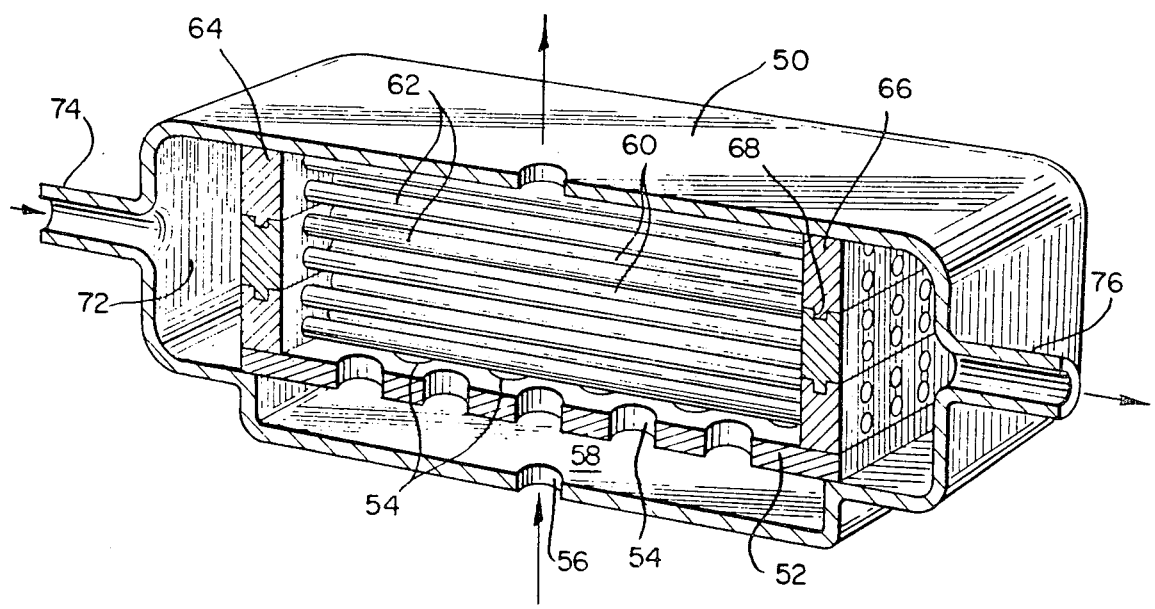
FIG. 12 is a side cross-sectional view of an alternative reactor means for carrying out the process of this invention.

FIG. 12 shows an alternative reactor construction useful in the present invention. The reactor comprises a shell 50 which houses a plate 52 having a plurality of holes 54 therein. The plate 52 extends above the entire internal cross-section of the shell 50 so that any gas entering through inlet 56 into plenum 58 must pass through the holes 54 in order to pass into chamber 60. The hollow tubes 62 are coated on the exterior and the interior surfaces with catalysts as described above in order to effect oxidation of ethylene to ethylene oxide. Tubes 62 extend across chamber 60 and are attached to plates 64 and 66. The plates 64 and 66 have a cross-section such as the tongue and groove shape 68 shown so that when the plates are placed upon each other, they form a seal between the plenum chamber 70 and the chamber 60 as well as the plenum chamber 72 and the chamber 60. An oxygen-containing gas enters inlet 74, passes through tubes 62 and exits through outlet 76. An ethylene-containing gas passes through inlet 56 into plenum 58, through openings 54 into chamber 60 and out outlet 78 to a means (not shown) for recovering ethylene oxide from the ethylene-containing gas.

Figure 13:
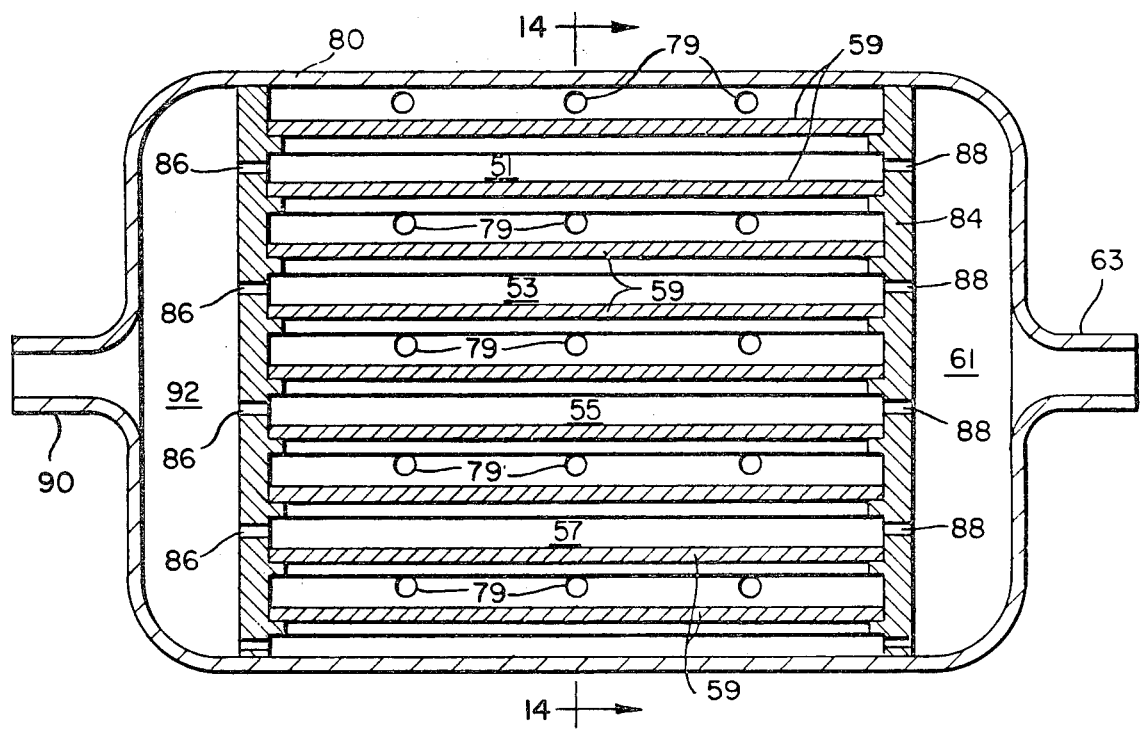
FIG. 13 is a front cross-sectional view of an alternative reactor means for carrying out the process of this invention.
Figure 14:
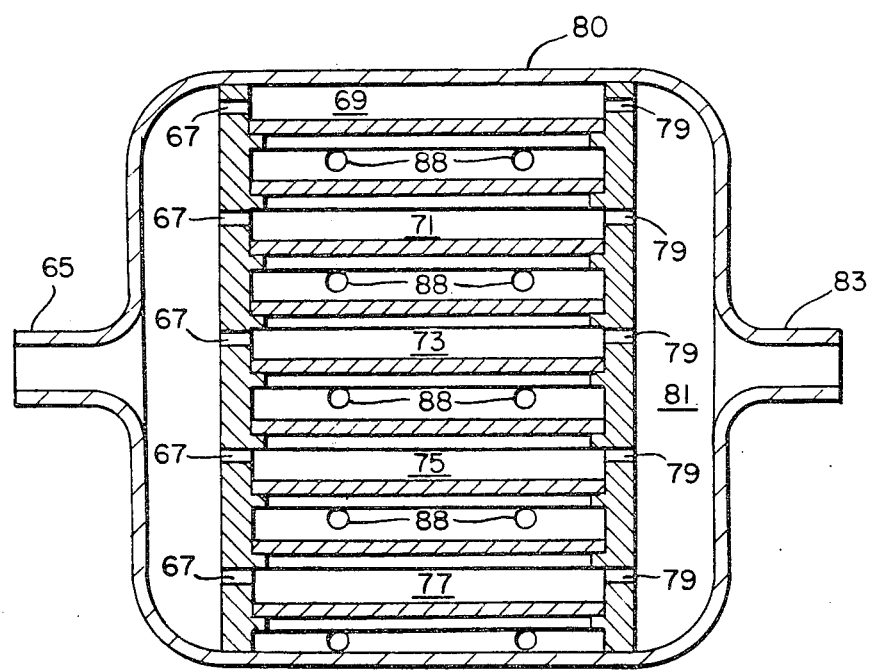
FIG. 14 is a side cross-sectional view of the reactor of FIG. 13 taken along line 14—14.

The reactor shown in FIGS. 13 and 14 utilizes a solid electrolyte in the form of plates rather than tubes. The reactor comprises a shell 80 having plates 82 and 84 provided with inlets 86 and outlets 88. Oxygen-containing gas enters the shell 80 through inlet 90, passes through plenum chamber 92 through inlets 86 and into chambers 51, 53, 55 and 57 to contact the catalyst on the plates 59. The oxygen-depleted gas passes through exits 88 into plenum 61 and out through outlet 63. An ethylene-containing gas enters shell 80 through inlet 65, passes through inlet 67 and into chambers 69, 71, 73, 75 and 77. In chambers 69 through 77, the ethylene-containing gas is converted to a ethylene oxide and the resultant gas product passes through exits 79 into plenum 81 and through outlet 83.

In the manner shown in FIG. 9, suitable electrical leads are attached to each of the catalytic surfaces of the reactor shown in FIGS. 10 through 14 in order to apply electrical energy to the solid electrolytes. Any conventional means for separating ethylene oxide from unconverted ethylene can be utilized in the present invention.

We claim:

1. The process for oxidizing ethylene to form ethylene oxide which comprises passing an ethylene-containing feed gas in contact with a first catalyst deposited on a first surface of a solid electrolyte and passing an oxygen-containing gas in contact with a second catalyst deposited on a second surface of said solid electrolyte, said first catalyst being capable of promoting the oxidation of ethylene to ethylene oxide, said second catalyst being capable of dissociating oxygen gas to form oxygen ions to contact said ethylene to form ethylene oxide and applying a voltage between said first and second catalysts through said solid electrolyte.

2. The process of claim 1 wherein said solid electrolyte comprises yttria stabilized zirconia.

3. The process of any one of claims 1 and 2 wherein said first catalyst comprises silver-containing metal composition.

4. The process of any one of claims 1 and 2 wherein said second catalyst comprises a platinum-containing metal composition.

5. The process of claim 1 wherein said solid electrolyte comprises calcia stabilized zirconia.

6. The process of claim 5 wherein said first catalyst comprises a silver-containing metal composition.

7. The process of claim 5 wherein said second catalyst comprises a platinum-containing metal composition.

* * * * *